United States Patent
Adachi et al.

(10) Patent No.: US 8,155,738 B2
(45) Date of Patent: Apr. 10, 2012

(54) COMPOSITION AND DEVICE STRUCTURE FOR IONTOPHORESIS

(75) Inventors: Hirotoshi Adachi, Tsukuba (JP);
Noriyuki Kuzumaki, Tsukuba (JP);
Tetsuya Arimoto, Tsukuba (JP);
Naruhito Higo, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 0 days.

(21) Appl. No.: 12/895,934

(22) Filed: Oct. 1, 2010

(65) Prior Publication Data

US 2011/0021972 A1   Jan. 27, 2011

Related U.S. Application Data

(60) Continuation of application No. 10/674,419, filed on Oct. 1, 2003, now abandoned, which is a division of application No. 09/651,272, filed on Aug. 30, 2000, now abandoned.

(30) Foreign Application Priority Data

Sep. 1, 1999   (JP) .................................... 11-246972

(51) Int. Cl.
| | |
|---|---|
| *A61N 1/30* | (2006.01) |
| *A61K 9/70* | (2006.01) |
| *A61K 9/22* | (2006.01) |
| *A61F 13/00* | (2006.01) |
| *A61M 35/00* | (2006.01) |

(52) U.S. Cl. .................... 604/20; 604/890.1; 604/891.1; 604/289; 602/57; 424/449; 424/402

(58) Field of Classification Search .................... 604/20, 604/289, 890.1, 891.1, 891.2; 602/57; 424/449, 424/402
See application file for complete search history.

(56) References Cited

U.S. PATENT DOCUMENTS

| | | | |
|---|---|---|---|
| 4,474,570 A | 10/1984 | Ariura et al. | |
| 4,973,303 A | 11/1990 | Johnson et al. | |
| 5,306,504 A | 4/1994 | Lorenz | |
| 5,312,326 A | 5/1994 | Myers et al. | |
| 5,648,399 A | 7/1997 | Friedman et al. | |
| 5,857,992 A | 1/1999 | Haak et al. | |
| 6,322,550 B2 * | 11/2001 | Iga et al. | ........................ 604/501 |
| 6,416,503 B1 | 7/2002 | Suzuki et al. | |
| 6,678,554 B1 | 1/2004 | Sun et al. | |
| 2004/0071765 A1 | 4/2004 | Adachi et al. | |

FOREIGN PATENT DOCUMENTS

| | | |
|---|---|---|
| EP | 0577034 A2 | 1/1994 |
| JP | 03-151982 A | 6/1991 |
| JP | 07-213628 A | 8/1995 |
| JP | 09-071541 A | 3/1997 |
| JP | 09-248344 A | 9/1997 |
| WO | 97/12644 | 4/1997 |
| WO | 00/62857 | 10/2000 |

OTHER PUBLICATIONS

L. Brannon-Peppas Medical Plastics and Biomaterials Magazine, Nov. 1997.*

* cited by examiner

*Primary Examiner* — Jason M Nolan
(74) *Attorney, Agent, or Firm* — Sughrue Mion, PLLC

(57) ABSTRACT

Device structure 100 for iontophoresis provides electrode 101 and electrically conductive layer 102. Electrically conductive layer 102 contains active ingredient D and basic water swelling methacrylate copolymer P1 and/or acidic water swelling methacrylate copolymer P2. Electrode 101 and electrically conductive layer 102 are placed into a hollow of backing 103 and electrode terminal 104 is connected to electrode 101 through backing 103. Adhesive layer 105 is set around backing 103, and liner 106 to be removed when using the device, is placed so as to cover the hollow of backing 103.

4 Claims, 2 Drawing Sheets

CONCENTRATION OF ADDED pH ADJUSTING AGENT (w/w%)

CONCENTRATION OF ADDED METHACRYLATE COPOLYMER E (%)

COMPOSITION AND DEVICE STRUCTURE FOR IONTOPHORESIS

BACKGROUND OF INVENTION

The present invention relates to a composition for iontophoresis and a device structure using it, more specifically, a composition for iontophoresis to deliver an active ingredient to an organism safely and efficiently using electric driving power and a device structure using it.

Iontophoresis is an accelerating system for transdermal absorption using electricity as an outside stimulus. The principal is that it accelerates penetration of the drug's molecules through the skin barrier based on the moving power of positively charged molecules and negatively charged molecules from the anode to the cathode and from the cathode to the anode, respectively, in the electric field generated between the anode and the cathode mainly by energizing with current (see Journal of Controlled Release, vol. 18, 213-220, 1992; Advanced Drug Delivery Review, 119, 1992; Pharmaceutical Research, vol. 3, pp. 318-326, 1986).

Iontophoresis is a method of making the charged drugs be absorbed in the body positively by electrochemical potential, for example, positively charged drugs are administered to the skin from the anode side. In this case, because the electricity flows through attached organs such as sweat glands and hair follicles which have less electric resistance in the horny layer, it is considered that drugs are delivered mainly through these channels to the epidermis, thereafter spread in the living epidermis, and move to the dermis or the vessel system. In addition, non-charged materials become to move by ions in the solvent through moving of water by the electric field. Thus, in the iontophoresis, electric repulsion and electric penetration play a significant role in addition to the passive diffusion for drug absorption.

On the other hand, it was found that pharmacokinetic control is important for the drugs which show potent bioactivity at a very small quantity and the system being capable for responding for strict dosing control has been required in order to control the adverse reactions to the minimum as well as to make drug efficacy show to the maximum. For example, synthesized narcotic analgesics have only narrow therapeutic range because they have not only a potent analgetic action but also cause significant adverse reactions such as respiratory depression. Calcitonin has an inhibitory action to bone quantity reduction and is used for treating osteoporosis or Paget's disease. The excessive dosing, however, cause the adverse reactions such as anorexia while they are needed to be frequently administered repetitively to increase their therapeutic effect. Most of the drugs are known, however, to be not absorbable since they are decomposed by digestive juices in the gastrointestinal tracts or hydrolized by decomposing enzymes of the gastrointestinal walls. Therefore, as for administration of these drugs, injection is usually conducted to avoid adverse reactions and because adequate efficacy control can not be expected by oral administration. Injections, however, give much pain to patients and become a burden since they can not be self-administered, even more so particularly in the case of the above described Calcitonin which is needed to be frequently administered repetitively.

Iontophoresis has been studied energetically as a new drug delivery system which can respond for such drug administration in the pharmaceutical field. That is, developing the drugs conventionally capable of being administered only as a injection to the formulation capable of being self-administered will allow medical treatment at home. Further, it is considered that particularly in supplementary therapies of endogenous compounds, more effective drug therapy can be realized taking the circadian rhythm of the living body into account since optional absorption patterns can be generated by controlling the energizing time precisely. Absorption control is also possible by controlling values of electric current.

General structure in the iontophoresis comprises a power source device, the electrodes of the electrically conductive layer connected to the power source device and the electrodes of the electrolyte reservoir. Further, the electrodes of the electrically conductive layer comprise electrodes and an electrically conductive layer, herein the electrode material and preparation of the electrically conductive layer affect greatly the drug efficacy. In order to design an effective drug delivery system in the iontophoresis, the physicochemical factors in the preparation, in particular, ionic strength, competitive ion species, pH, molecular weight (size), concentration and the number of charges and the like in the preparation, are particularly significant as a pharmaceutical approach. Particularly, the electrodes of the electrically conductive layer add the absorption and stability of drugs and stability of the administrated sites while pH of the preparation of electrically conductive layer is a significant factor in order to make iontophoresis effective at the maximum.

Influences of pH on the drug absorption are shown in many references, e.g., Advanced Drug Delivery Review, vol. 18, pp. 379-394, 1996. As a conventional means of iontophoresis, it is described that the drug delivery efficiency with electric current is elevated by increasing the drug ratio in the dissociation state. However, it is known that the materials in the preparation to control the pH include the ion species which have the similar polarity to the drug (competitive ions) causing to reduce the drug delivery ratio substantially.

Further, Japanese Patent Laid-Open Publication No. 9-235230 discloses that pH is adjusted to weak acid region by adding an organic acid to improve the stability of prostaglandin $E_1$ in the electrically conductive layer for iontophoresis. The organic acids are, however, polar materials similar to prostaglandin $E_1$, therefore they can not avoid competition with the drugs when used together.

Further, Japanese Patent Laid-Open Publication No. 9-504191 discloses that the cathode reservoir is adjusted to less than pH 4 and the anode reservoir is adjusted to pH 4-10 in order to reduce stimulation and resistance to skin. As pH adjusting materials or buffer agents used for these purposes, acidic or basic materials with low molecular weight are described. These pH adjusting materials or buffer agents have approximately similar or below the molecular weight of the drugs, therefore they have the problem that they lower the drug delivery rate and reduce the drug absorption when being existed together with drugs.

On the other hand, the study on composition for iontophoresis has proceeded and WO No. 96/34,597 discloses a pH adjusting method using an anion-exchange resin or a cation-exchange resin, e.g. it is disclosed that pH adjustment in the solution containing a drug is conducted with pretreatment by using a hydroxide of the anion-exchange resin as a pH adjusting agent for the solution containing a cationic drug and using the cation-exchange resin having an acidic region as the pH adjusting agent for the solution containing a anionic drug. These operation of pH adjustment is, however, complicated and not practical in terms of quality assurance owing to drug adhesion to the resin, or the like.

Further, in iontophoresis using inactive electrodes such as carbon, platinum and titanium, hydrogen ions and oxygen gas generate at the anode side, and hydroxyl ions and hydrogen gas generate at the cathode side during energizing with current. Thus, at the cathode side, pH of the electrically conductive layer rapidly increases during energizing resulting in reduction of the drug delivery rate and therefore extreme reduction of drug absorption.

On the other hand, in the iontophoresis using active electrodes represented as silver and silver chloride, oxidation or reduction occurs at the voltage lower than that for water electrolysis during energizing. At the anode side, silver electrode is usually used and the electrically conductive layer contains the counter materials such as a chloride ion required for the oxidation or reduction with electrodes. That is, the metal ions (e.g., silver ions) eluted from the anode side during energizing react with the counter ions (e.g., a chloride ion in chloride salts such as sodium chloride and quaternary ammonium chloride such as cholestyramine) contained in the electrically conductive layer, and generate insoluble precipitate (e.g. silver chloride). These practically down-regulate the metal ions' transfer to the skin followed by less generation of protons compared with the case of inactive electrodes, thus they have also high level of safety to the skin. Although proton transfer to the skin is less than the case of inactive electrodes, protons in the electrically conductive layer (containing protons depending on the reservoir's pH) at the anode side gradually transfer to the skin during energizing with current causing pH elevation of the electrically conductive layer. This changes dissociation of the drug and affects the drug absorption particularly with long time energizing with current. No solution has been found yet for means to control those pH changes occurred during energizing with current.

Further, in Japanese Patent Laid-Open Publication No. 7-213628, aminoacryl methacrylate copolymer is described as an example of a film base for the purpose of controlling the drug release. The function is, however, limited to the drug release control and there is no description about the composition for iontophoresis for effective delivery of the drug.

Therefore, the purpose of the present invention is to provide a composition for iontophoresis and the device structure which enables to maintain stable drug absorption without decreasing the drug transfer rate.

SUMMARY OF THE INVENTION

The present inventors have been investigating earnestly the pH adjusting ingredient for iontophoresis excellent in drug release without decreasing the transfer rate or uniformity and dispersion at preparation, further the influence on the base components. As a result, we found that good electrical conductivity as well as efficient and stable drug absorption for long time can be obtained by controlling pH scattering, uniformity and dispersion at preparation, further pH variation during energizing with current, by using a water swelling polymer showing pH dependent solubility in a electrically conductive layer using iontophoresis, without decreasing the drug delivery rate, enabling safe drug delivery to the living body, and thus we completed the present invention.

Specifically, a composition for iontophoresis and the device structure can be obtained which is excellent in preparativity, properties and stability of the composition, controls the pH variation during energizing with current, thus enable the percutaneous drug administration repetitively with remarkably high biological efficiency, by using at least either weakly basic or weakly acidic swelling polymer, e.g., a water swelling polymer comprising a polyamine of primary, secondary or tertiary amines and a water swelling polymer comprising a carboxylic acid.

Namely, the invention is a composition for iontophoresis comprising at least one of partially ionized active ingredients and a water swelling polymer which has a pH adjusting function in the electrically conductive layer.

Further, the present invention is an electrically conductive layer comprising the above described composition for iontophoresis.

Further, the present invention is a device structure for iontophoresis which is provided with the electrically conductive layer containing at least one of partially ionized active ingredients and a water swelling polymer having a pH adjusting function, and electrodes which supply electric current.

DESCRIPTION OF THE PREFERRED EMBODIMENTS

Figure 1:
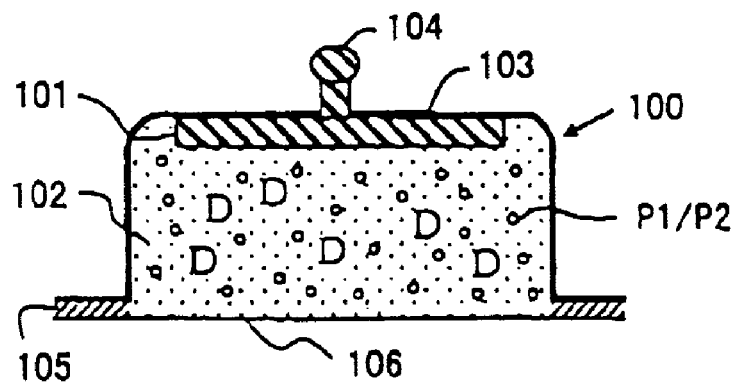
FIG. 1 is a cross section showing one example of the device structure of the present invention.

The present invention will be described in details, herein after.

In the invention, a water swelling polymer is preferably at least either a weakly basic or weakly acidic polymer which shows a characteristic of pH-dependent solubility.

A weakly basic methacryl acid copolymer is preferably used to adjust pH at the anode side to 4-7 and pH at the cathode side to 6-9. Therefore, around the pH to be adjusted, the pH variation depending on the amount of an added pH adjusting agent should be preferably small for the minimum scattering at preparation.

As such a weakly basic polymer, a water swelling polymer comprising a polyamine of primary, secondary or tertiary amines is preferable.

Water swelling polymers comprising a polyamine of primary, secondary or tertiary amines include, for example, a copolymer of basic methacrylic acid and methacrylate.

Herein, the functional groups of the above described primary, secondary or tertiary amine are optionally selected to specify the pH-adjusting region and a dimethylaminoethyl group is particularly preferable when adjusting pH around weakly acidic to neutral regions. As methacrylate, an ester group such as a methyl, ethyl, propyl or butyl group is selected to give the characteristic of pH-dependant solubility.

A basic methacrylate copolymer is preferably soluble at lower pH than around weakly acidic to neutral regions and hardly soluble at higher pH than that. Herein, the term "soluble" means that the polymer is apparently dissolved and the term "hardly soluble" means that it is dispersed.

The basic methacrylate copolymer may use, e.g. aminoalkyl methacrylate copolymer E (Eudragit E100, Eudragit EPO, E35L, etc.).

In the case that the water swelling polymer contain a basic methacrylate copolymer, particularly aminoalkyl methacrylate copolymer E, further, this contains preferably at least either hydrochloric acid or a weakly acidic material with at least one pKa within a range of 3 to 9. When using particularly a cationic drug, a buffer composition which minimizes influence on the drug delivery rate can be obtained. Specifically, these can reduce scattering of the pH at preparation, and further add a function for an electrode reaction with an active electrode such as silver by adding hydrochloric acid.

Weakly acidic materials in this case preferably use at least one selected from the group of organic acids and acidic amino acids. Examples of organic acids and acidic amino acids include citric acid, acetic acid, glacial acetic acid, sodium dihydrogen-phosphate, lactic acid, succinic acid, maleic acid, benzoic acid, tartaric acid, ascorbic acid, erysorbic acid, sorbic acid, mesylic acid, boric acid, gluconic acid, fumaric acid, phthalic acid, oxalic acid, malic acid, glutamic acid, asparatic acid and the like. Further, a buffer action can be improved by appropriately adding a buffer agent and amino acids.

On the other hand, an acidic methacryl acid copolymer is preferably the one which is soluble at higher pH than around weakly acidic to weakly basic regions and hardly soluble at lower pH than that. The acidic methacryl acid copolymer may use at least one of methacryl acid copolymer L and methacryl acid copolymer S. In this case, the polymer further contains a weakly basic material having at least one pKa within the range of 3-10, and when using particularly an anionic drug, a buffer composition which minimized influence to the drug delivery rate can be obtained. Specifically, these can reduce scattering of the pH at preparation, and further add a function for an electrode reaction with an active electrode such as silver by adding hydrochloric acid.

Such weakly basic materials preferably use e.g., at least one of salts of organic acids and basic amino acids. Salts of organic acids or basic amino acids include: e.g., salts of organic acids such as citric acid, acetic acid, glacial acetic acid, sodium dihydrogenphosphate, lactic acid, succinic acid, maleic acid, benzoic acid, tartaric acid, ascorbic acid, erysorbic acid, sorbic acid, mesylic acid, boric acid, gluconic acid, fumaric acid, phthalic acid, oxalic acid or malic acid; disodium hydrogenphosphate; and arginine, lysine, histidine or the like. Further, a buffer action can be improved by appropriately adding a buffer agent and amino acids.

In the present inventive composition for iontophoresis, a weakly acidic polymer is preferably a water swelling polymer comprising carboxylic acids.

A water swelling polymer comprising carboxylic acids includes a weakly acidic methacrylate copolymer as a preferable example.

A weakly acidic polymer and a methacrylate copolymer used in the present inventive composition for iontophoresis are used e.g., to adjust pH at the anode side to 4-7 and pH at the cathode side to 6-9, preferably, suitable for the pH adjustment at the cathode side. Herein, an ester group of methacrylate is selected from a methyl, ethyl, propyl or butyl group. Such a weakly acidic methacrylate copolymer are e.g., methacrylate copolymer L or methacrylate copolymer S (Eudragit L, Eudragit S etc.). These weakly acidic methacrylate copolymers are soluble (swelling) at higher pH (e.g., around pH 6-7) than around weakly acidic to weakly basic regions and hardly soluble at lower pH than that. Particularly, this type polymer is used not only as a pH adjusting material, but also effective in a pH preserving material in iontophoresis. For example, when using an inactive electrode, phenomena such as rapid elevation of the pH accompanied with generation of hydroxide ion observed in the electrically conductive layer of the cathode side, can be prevented by adding an acidic methacrylate copolymer in dispersive condition, and therefore the initial pH is stably kept during energizing with current.

Herein, in the case that the active ingredient of the present inventive composition for iontophoresis is a cationic material, a basic methacrylic acid polymer or a mixture of a basic methacrylate copolymer and an acidic methacrylate copolymer is preferably used as a water swelling polymer, while in the case that the active ingredient is an anionic material, an acidic methacrylate copolymer or a mixture of a basic methacrylate copolymer and an acidic methacrylate copolymer is preferably used as a water swelling polymer.

Further when using in combination with these basic or acidic methacrylate copolymer and particularly with use of a water swelling polymer in dispersive condition, the pH variation during energizing with current around pH5-7 can be controlled and therefore the drug absorption can be maintained more effectively. Specifically, the following phenomena can be avoided; the pH variation of the electrically conductive layer during energizing with current observed at the anodic or cathodic side when using an active electrode; the rapid pH change of the electrically conductive layer accompanied with generation of hydrogen ion or hydroxide ion observed at the anodic or cathodic side when using an inactive electrode.

The average molecular weight of the water swelling polymer used in the present invention is preferably 1,000-10,000,000 dalton, more preferably 10,000-1,000,000 dalton even more preferably 100,000-1,000,000 dalton. This kind of polymer is desirably a non-moving material actually not to affect the absorption of the active ingredient. Further, it is desirable that the average molecular weight of the water swelling polymer used in the invention is preferably 1-100,000 times, more preferably 2-50,000 times, and most preferably 100-10,000 times to the molecular weight of the active ingredient since the swelling polymer becomes a competitive ion species when it shows similar polarity to that of the active ingredient drug.

Incidentally, the followings often become competitive ions against the drug and can not mostly give efficient absorption such as the water swelling polymer of the invention: the organic acids or their salts with low molecular weight (about 200 or less) used as a generally basic pH adjusting material; amines (e.g. ammonium hydroxide, ammonia, tromethamine, meglumine, triethanolamine, diethanolamine, monoethanolamine, triisopropanolamine, diisopropanolamine and monoisopropanolamine); and basic or acidic amino acids.

Although the content of the water swelling polymer in the present inventive composition for iontophoresis is not specifically limited if the content allow the objective pH to be adjusted or maintained, 0.001-50.0% (w/w) based on the whole weight of the composition is preferable and 0.01-20.0% (w/w) is particularly preferable. In such ranges, it does not affect the performance of the electrically conductive layer (such as gel property and drug release). Further, the following effects can be additionally obtained by adding a water swelling polymer in the base solution; improving effect on drug absorption; improving effect on electrically conductive layer properties (e.g. maintaining formation of the base material, viscoelasticity, adherence, stability, etc.), drug release control and stability-improving effect in addition to the pH adjusting effect of the base material.

The used active ingredients containing in the present inventive composition for iontophoresis are not particularly limited to the types of drugs and their salts, adaptation of each drug and the like. For example, the following drugs are used: antibiotics, antifungal agents, antitumor agents, cardiotonic drugs, antiarrhythmic agents, vasodilator drugs, antihypertensive agents, diuretics, hypotensive diuretics, circulatory drugs, anti-platelet agents, hemostatic drugs, hypolipidemic drugs, antipyretic analgesic antiphlogistics, antirheumatic drugs, muscle relaxants, antitussive and expectorant drugs, antiulcer agents, sedative drugs, antiepileptic drugs, antidepressant drugs, antiallergic agents, antidiabetic drugs, antituberculous agents, hormone agents, antinarcotics, restrainers of bone resorption, inhibitory agents of neovascularization, local anesthetics, and the like. In the present invention, use of hydrochloride of these active ingredients is particularly preferable.

The kinds and number of these ingredients are not particularly limited, and different active ingredients may be contained in each electrode structure to enhance the pharmacological effects. Further, the two electrode structures particularly preferably contain at least one or more of the same active ingredients.

As the antibiotics, for example, gentamicin sulfate, lipidomycin, sisomicin sulfate, tetracycline hydrochloride, ampicillin, cefalotin sodium, cefotiam dihydrochloride, cefotiam dihydrochloride, tienamycin, sulfazecin, streptomycin sulfate, kanamycin sulfate, rifampicin, vancomycin hydrochloride, ofloxacin, cefoselis sulfate, and the like may be used.

As the antifungal agents, for example, amphotericin B, itraconazole, fluconazole, miconazole, 2-[(1R,2R)-2-(2,4-difluorophenyl-2-hydroxy-1-methyl-3-(1H-1,2,4-triazole-1-yl)propyl)-4-[4-2,2,3,3-tetra fluoropropoxy]-phenyl]-3(2H, 4H)-1,2,4-triazolon, and the like may be used.

As the antitumor agents, for example, bleomycin hydrochloride, tegafur, actinomycin D, mitomycin C, adriamycin, fluorouracil, 6-mercaptopurine, cytarabine, procarbazine, doxorubicin hydrochloride, methotrexate, tamoxifen citrate, and the like may be used.

As the cardiotonic drugs, for example, trans-bioxocamphor, theophylol, dopamine hydrochloride, dobutamine hydrochloride, ubidecarenone, and the like may be used.

As the antiarrhythmic agents, for example, propranolol hydrochloride, oxyprenolol hydrochloride, procainamide hydrochloride, lidocaine, phenyloin, metoprolol tartrate, verapamil hydrochloride, diltiazem hydrochloride and the like may be used.

As the vasodilator drugs, for example, oxyfedrine hydrochloride, tolazoline hydrochloride, bamethan sulfate, nicardipine hydrochloride, verapamil hydrochloride, papaverine hydrochloride, and the like may be used.

As the antihypertensive agents, for example, hydralazine hydrochloride, budralazine, prazosin hydrochloride, doxazocine misilate, carteolol hydrochloride, clonidine hydrochloride, enalaprilmaleate, captopril, delaprilhydrochloride, manidipine hydrochloride, pinasidil, minoxidil, losartan, candesartan cilexetil, balsartan, terumisartan, irubesartan, and the like may be used.

As the diuretics, for example, acetazolamide, methazolamide, chlorothiazide, furosemide, triamterene, amiloride, aminometrodine, and the like may be used.

As the following hypotensive diuretics, for example, pentolinium, hexamethonium bromide, and the like may be used.

As the circulatory drugs, for example, alprostadil, limaprost, sodium ozagrel, clopidogrel sulfate, belaprost, ciprosten, iloprost, ataprost, clinprost, ethyl icosapentate, etilefrine hydrochloride, dihydroergotamine mesylate, pamicogrel, tranilast, probucol, candesartan cilexetil, sodium citrate, heparin, low molecular weight heparin, nifedipine, efonidipine hydrochloride, diltiazem hydrochloride, tranilast, and the like may be used.

As the anti-platelet agents, for example, ticlopidine, satigrel, limaprost alfadex, clinprost, clopidogrel sulfate, cibrafiban, epchibatid, tilofiban hydrochloride, sarpogrelate hydrochloride, zemilofiban hydrochloride, orbofiban acetate, isubogrel, cilostazol, aspirin, abkicimab, GpIIb/IIIa antagonist (e.g., (S)-4-(4-guanidinobenzoylamino)-acetyl-3-[3-(4-guanidinobenzoylamino)]propyl-2-oxo-piperadine-1-acetate dihydrochloride) and the like may be used.

As the hemostatic drugs agents, for example, epinephrine, menadione sodium bisulfite, acetomenaphthone, tranexamic acid, and the like may be used.

As the hypolipidemic drugs, for example, pravastatin sodium, sinvastatin, fluvastatin sodium, cerivastatin, atluvastatin, and the like may be used.

As the antipyretic analgesic antiphlogistics, for example, ketoprofen, aspirin, sodium salicylate, sulpyrine, indomethacin, diclofenac sodium, loxoprofen sodium, felbinac, zaltoprofen, piroxicam, nimeslid, meloxicam, celexicob, tialamide, emorfazone, buprenorphine, eptazocine hydrobromide, pentazocine, butorphanol tartrate, tramadol hydrochloride, ketolorac, meperidine hydrochloride, morphine hydrochloride, morphine sulfate, hydromorohine, fentanyl citrate, fentanyl hydrochlorate, fentanyl, sufentanyl, mofezolac and the like may be used.

As the antirheumatic drugs, for example, methotrexate hydrochloride, gold sodium thiomalate, auranofin, bucillamine, D-penicillamine, actarit, lobenzarit, mizoribine, salazosulfapyridine, tacrolimus hydrate, dexamethasone phosphate, betamethasone phosphate, prednisolone sodium succinate, and the like may be used.

As the muscle relaxants, for example, pridinol mesilate, tubocurarine chloride, eperisone hydrochloride, tizanidine hydrochloride, chlorphenesin carbamate, tolperisone hydrochloride, dantrolene hydrochloride, baclofen, lamperizon hydrochloride, and the like may be used.

As the antitussive and expectorant drugs, for example, ephedrine hydrochloride, codeine phosphate, picoperidamine hydrichloride, ambroxol, bromhexine hydrochloride, salbutamol sulfate, tulobuterol hydrochloride, formoterol fumarate, azelastine hydrochloride, ketotifen fumarate, picoperidamine, and the like may be used.

As the antiulcer agents, for example, ornoprostil, cimetidine, famotidine, ranitidine hydrochloride, metoclopramide, omeprazole, lansoprazole, and the like may be used.

As the sedative drugs, for example, chlorpromazine hydrochloride, atropine sulfate, fluphenazine enanthate, and the like may be used.

As the antiepileptic drugs, for example, sodium phenyloin, ethosuximide, and the like may be used.

As the antidepressant drugs, for example, amitriptyline hydrochloride, imipramine hydrochloride, clomipramine hydrochloride, desipramine hydrochloride, maprotiline hydrochloride, phenelzine sulfate, and the like may be used.

As the antiallergic agents, for example, diphenhydramine hydrochloride, tripelennamine hydrochloride, clemizole hydrochloride, d-chlorpheniramine maleate, cyproheptadine hydrochloride, ketotifen fumarate, epinastine, tacrolimus hydrate, and the like may be used.

As the antidiabetic drugs, for example, glimidine, sodium, glypizide, metformin, tolbutamide, chlorpropamide, glibenclamide, acetohexamide, midaglizole, glimepirid, senaglinid, repaglinid, pioglitazone hydrochloride, and the like may be used.

As the antituberculous agents, for example, streptomycin sulfate, kanamycin sulfate, isoniazid, ethambutol hydrochloride, pyrazinamide, and the like may be used.

As the hormone agents, for example, β-estradiol, testosterone enanthate, prednisolone succinate, dexamethasone sodium phosphate, methimazole, and the like may be used.

As the antinarcotics, for example, levallorphan tartrate, nalorphine hydrochloride, protamine, naloxone, and the like may be used.

As the restrainers of bone resorption, for example, aminomethylene bisphosphonic acid (sulfur-containing alkyl), laroxifen, alendoronate sodium, incadronate disodium, tiboron, simadronate, risedronate, clodronatedisodium, farecalcitriol, calcitriol, alfacalcitriol, didronel sodium, ipriflavone, minodronic acid, and the like may be used.

As the inhibitory agents of neovascularization, for example, steroids for suppression of neovascularization [Science, vol. 221, p. 719, (1983)], fumagirol derivatives [monochloroacetylcarbamoyl fumagirol, dichloroacetyl-carbamoyl fumagirol, etc. (Publication of European Patent Application No. 357061, ibid. No. 359036, ibid. No. 386667, and ibid. No. 415294)] and the like may be used.

As the local anesthetic, for example, lidocaine hydrochloride, procaine hydrochloride, benzocaine hydrochloride, ethydrocaine hydrochloride, prilocalne hydrochloride, dibucaine hydrochloride, bupivacaine hydrochloride, cocaine hydrochloride, ethyl aminobenzoate, orthocaine hydrochloride, oxethazaine hydrochloride, mepivacaine hydrochloride, and the like may be used.

Other active ingredients include compounds having pharmacological activities such as peptides, protein and DNA, oligosaccharides. When indicating by using symbols of amino acids, peptides, etc. in this specification, these are based on the symbols by IUPAC-IUB commission on Biochemical Nomenclature or the conventional symbols in this field. Further, if an amino acid can have the optical isomers, this indicates the L-form if not specified.

The following peptides may be used.

Luteinizing hormone releasing hormone (LH-RH), or its derivatives having actions similar to LH-RH, for example, polypeptides represented as the following formula (I);

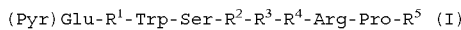
(Pyr)Glu-R$^1$-Trp-Ser-R$^2$-R$^3$-R$^4$-Arg-Pro-R$^5$  (I)

[wherein R$^1$ is His, Tyr, Trp or p-NH$_2$-Phe; R$^2$ is Tyr or Phe; R$^3$ is Gly or a D-type amino acid residue; R$^4$ is Leu, Ile or Nle; R$^5$ is Gly-NH—R$^6$ (R$^6$ is H or a lower alkyl group which may have a hydroxyl group), or NH—R$^6$ (R$^6$ is the same as the above description)] or their salts [see U.S. Pat. Nos. 3,853, 837, 4,008,209 and 3,972,859, British Patent No. 1423083 and Proceedings of the National Academy of Science, vol. 78, 6509-6512, 1981].

LH-RH antagonists, for example, polypeptides represented as the following formula (II):

N-α-t-butoxycarbonyl-O-benzyl-Ser-Trp-Ser-Tyr-X$_1$-

Leu-Arg-Pro-GlyNH$_2$  (II)

[wherein X$_1$ is D-Ser or D-Trp] or their salts [see U.S. Pat. Nos. 4,086,219, 4,124,577, 4,253,997, and 4,317,815].

Insulin; somatostatin or somatostatin derivatives, for example, polypeptides represented as the following formula (III):

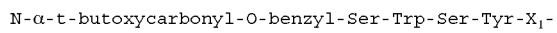
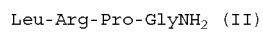
(III)
H-L-Ala-Y-L-Cys-L-Lys-Z-L-Phe-L-Phe-D-Trp-L-Lys-L-
Thr-L-Phe-L-Thr-L-Ser-L-Cys-OH

[wherein Y is D-Ala or D-Ser or D-Val; Z is Asn or Ala] or their salts [see U.S. Pat. Nos. 4,087,390, 4,093,574, 4,100, 117, and 4,253,998].

Adrenocorticotrophic hormone (ACTH); melanocyte-stimulating hormone (MSH), thyrotropin releasing hormone (TRH), or their derivatives, for example, compounds represented as the following formula (IV):

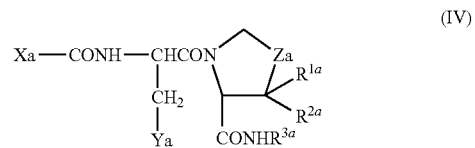

[wherein Xa is a 4, 5 or 6-membered heterocyclic group; Ya is imidazole-4-yl or 4-hydroxyphenyl; Za is CH$_2$ or S; R$^{1a}$ and R$^{2a}$ are hydrogen or the same or different lower alkyl groups; and R$^{3a}$ is an aralkyl which may have hydrogen or substituents] or their salts [see Japanese Patent Laid-Open Publication No. 50-121273 and Japanese Patent Laid-Open Publication No. 52-116465].

Parathyroid hormone (PTH) or its derivatives, for example, peptide represented as the following formula (V):

R$^{1'}$-Val-Ser-Glu-leu-R$^{2'}$-His-Asn-R$^{3'}$-R$^{4'}$-R$^{5'}$-His-

Leu-Asn-Ser-R$^{6'}$-R$^{7'}$-Arg-R$^{8'}$-Glu-R$^{9'}$-Leu-R$^{10'}$-R$^{11'}$-

R$^{12'}$-Leu-Gln-Asp-Val-His-Asn-R$^{13'}$  (V)

[wherein R$^{1'}$ is Ser or Aib; R$^{2'}$ is Met or a natural fat-soluble amino acid; R$^{3'}$ is Leu, Ser, Lys or an aromatic amino acid; R$^{4'}$ is Gly or a D-amino acid; R$^{5'}$ is Lys or Leu; R$^{6'}$ is Met or a natural fat-soluble amino acid; R$^{7'}$ is Gly or a basic amino acid; R$^{5'}$ is Val or a basic amino acid; R$^{5'}$ is Trp or 2-(1,3-dithiolane-2-yl) Trp; R$^{10'}$ is Arg or His; R$^{11'}$ is Lys or His; R$^{12'}$ is Lys, Gln or Leu; R$^{13'}$ is Phe or Phe-Nh$_2$] or their salts (see Japanese Patent Laid-Open Publication Nos. 5-32696 and 247,034/96, EP Laid-Open Publication Nos. 510662, 477885, and 539491); peptide fragments etc., at N-terminal (1→34 position) of human type PTH (herein after, abbreviated as hPTH (1→34)) [see G. W. Tregear et al. Endocrinology, 93, pp. 1349-1353, (1973)]; and vasopressin and vasopressin derivatives {desmopressin [see Journal of Japan Endocrinology Society, vol. 54, No. 5, 676-691 (1978)]}.

Oxitocin; calcitonin and their derivatives having actions similar to calcitonin, for example, compounds represented as the following formula (VI):

(VI)

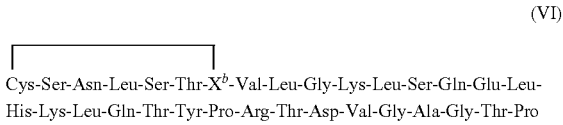
Cys-Ser-Asn-Leu-Ser-Thr-X$^b$-Val-Leu-Gly-Lys-Leu-Ser-Gln-Glu-Leu-
His-Lys-Leu-Gln-Thr-Tyr-Pro-Arg-Thr-Asp-Val-Gly-Ala-Gly-Thr-Pro

[wherein X$^b$ is 2-aminosuberic acid] or their salts (glucagon, gastrin, secretin, cholecystokinin, and angiotensin) [see Endocrinology, 131/6, 1885-2890, 1992].

Enkephalin and its derivatives, for example, peptides represented as the following formula (VII):

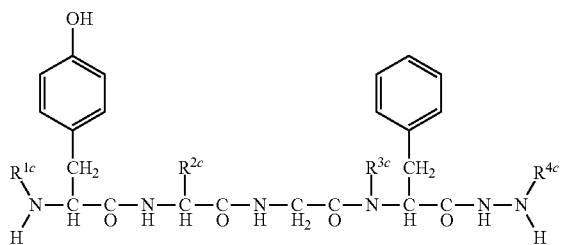

(VII)

[wherein $R^{1c}$ and $R^{3c}$ are hydrogen or a $C_{1-6}$ alkyl group; $R^{2c}$ is hydrogen or a D-α-amino acid; and $R^{4c}$ is hydrogen or an aliphatic acyl group which may be substituted with $C_{1-8}$] or their salts (oligopeptides, endorphine, etc.) (see U.S. Pat. No. 4,277,394 and EP Laid-Open Publication No. 31,567).

Kyotorphine; interleukin (I to XI); tuftsin; thymopoietin; thymic humoral factor (THF); blood thymic factor and their derivatives, for example, peptides represented as the following formula (VIII):

```
PGlu-Xd-Lys-Ser-Gln-Yd-Zd-Ser-Asn-OH   (VIII)
```

[wherein Xd is L- or D-Ala; Yd and Zd are Gly or a $C_{3-9}$ D-amino acid, respectively] or their salts (see U.S. Pat. No. 4,229,438); and other thymic hormones [for thymosin α1 and β4, thymic factor X, etc., see Igakuno Ayumi (Progress in Medicine) vol. 125, No. 10, pp. 835-843 (1983)].

The drugs, for example, motilin, dynorphin, bombesin, neurotensin, caerulein, bradykinin, urokinase, substance P, polymyxin B, colistin, gramicidin, bacitracin, protein synthesis-stimulating peptides (see British Patent No. 8232082), gastrin-inhibitory peptide, vasoactive intestinal polypeptide (VIP), platelet-derived growth factor (PDGF), growth hormone releasing hormone (GRF, somatoliberin), and the like, may be used.

These physiologically active peptides may use origins of human as well as those of other animals, for example, cattle, pig, chicken, salmon, eel, and chimeras between human and these animals. Further, these can use active derivatives in which a partial structure was modified. For example, insulin is an origin of pig and calcitonin is origins of pig, chicken, salmon, eel and chimeras between human and salmon. Peptides (see Endocrinology, 131/6, 2885-2890, 1992)) represented as the following formula (IX) may be used:

```
Cys-Gly-Asn-Leu-Ser-Thr-Cys-Met-Leu-Gly-Lys-Leu-
Ser-Gln-Glu-Leu-His-Lys-Leu-Gln-Thr-Tyr-Pro-Arg-
Thr-Asn-Thr-Gly-Ser-Gly-Thr-Pro   (IX)
```

The content of the active ingredient depends on the kind and activity of the active ingredient, and optionally selected relating to the weight of the composition for iontophoresis of the present invention and other components.

The composition for iontophoresis of the invention can give a device structure for iontophoresis capable of maintaining stable drug absorption without decreasing the drug transfer rate by such composition.

Details of the present invention will be described as follows referring the drawings if necessary. FIG. 1 is a cross section showing an example of the device structure of the present invention. As shown in FIG. 1, device structure 100 is provided with electrode 101 and electrically conductive layer 102. Electrically conductive layer 102 contains Active ingredient D and weakly basic water swelling methacrylate copolymer P1 and/or weakly acidic water swelling methacrylate copolymer P2. Herein, P1 and P2 are in the swelling condition (apparently dissolution condition) or the dispersion condition. Electrode 101 and electrically conductive layer 102 are set at the hollow of backing 103 and electrode 101 is connected to the terminal of electrode 104 through backing 103. Adhesive layer 105 is set around backing 103 and liner 106 which is to be put away when using the device is set so that it covers the hollow of backing 103.

Further, the water swelling polymer in the composition for iontophoresis of the present invention is also effective as a pH maintaining material in the structure for iontophoresis. For example, the phenomenon such as rapid pH reduction of the electrically conductive layer accompanied with generation of hydrogen ions observed in the anodic side when using an inactive electrode, can be controlled to the initial pH stably even during energizing with current by adding a basic methacrylate copolymer at the dispersion condition.

Further, to the composition for iontophoresis of the present invention, a surfactant can be added and an adjustable pH range can be extended by the water swelling polymer. Non-ionic surfactants can be used as such surfactants, e.g. polyoxyethylene hydrogenated castor oil 60, polyoxyethylene sorbitan monoolate, polyoxyethylene sorbitan monolaurate, polyoxyethylene lauryl ether, polyoxyethylene octylphenyl ether, polyoxyethylene nonylphenyl ether, polyoxyethylene polyoxypropylene glycol, polysorbate, sucrose fatty acid ester. These may be used each alone, or two or more of them may be combined to be used.

When adding the surfactant to the composition for iontophoresis of the present invention, the surfactant content is preferably 0.0001-20.0% (w/w) based on the whole weight of the composition for iontophoresis.

Further, the material which increases the dissolution of the above described basic or acidic methacrylate copolymer also can be optionally added to the composition for iontophoresis of the present invention.

The electrically conductive layer of the present invention, comprises the composition for iontophoresis of the present invention.

The electrically conductive layer of the present invention preferably comprises a gel, a solution type and the like.

As for a gel, although not limited to, an electrically conductive hydrophilic gels are preferably used, and synthesized polymers such as polyacrylic acid, sodium polyacrylate, methoxyethylene maleic anhydride copolymer, isobutylene maleic anhydride copolymer, isobutylene maleic acid copolymer, sodium N-vinylacetamide acrylate copolymer, N-vinylacetamide crosslinking form, carboxyvinyl polymer, polyvinyl alcohol, polyvinyl pyrrolidone, polyacrylamide; polysuccharides such as agar, starch, mannan, xanthan gum, locust be an gum, carrageenin, gellan gum, tamarind gum, curdlan, pectin, agarose, guar gum, alginic acid, sodium alginate, tara gum, karaya gum, acacia gum, dextran, cellulose, and their derivatives; gelatins and the like may be exemplified. These may be used alone, or two or more of them may be used in combination. Combination of these gels with a methacrylate copolymer in the composition for iontophoresis of the present invention increases the adhesion to the surface of the organism (e.g. the skin) and improves the properties such as adherence related to conductivity in iontophoresis.

Further, electrically conductive layer of the present invention may optionally contain electrolyte, pH adjusting agent, buffer, skin-protective agent, stimulation-relaxing agent, stabilizer, thickner, wetting agent, surfactant, solubilizer, solubilizing agent, wet-keeping agent, absorption accelerator, adhesives, adhesion-giving agent, antiseptic, and the like, provided that its performance is not affected.

Herein, the content of the composition for iontophoresis of the present invention (a water swelling polymer, organic acids and the like) in the electrically conductive layer of the present invention is preferably 0.001-50% (w/w) based on the whole weight of the electrically conductive layer.

Next, the device structure for iontophoresis of the present invention will be explained.

The device structure for iontophoresis of the present invention is provided with an electrically conductive layer for iontophoresis comprising the composition for iontophoresis of the present invention and an electrode which supplies the electric current to the above described electrically conductive layer.

The device structure for iontophoresis of the present invention is not limited to the device structure or distribution state of the active ingredient such as: (1) a matrix type structure (as shown in FIG. 1) wherein the active ingredient is dispersed, (2) a reservoir type structure provided with: a semipermeable membrane to retain the electrically conductive hydrophilic layer between the electrically conductive layer and the skin in a matrix type structure; a permselective membrane to control the transfer of materials; a control membrane to regulate the drug penetrating and the like. (3) a lamination type structure provided with: a drug retaining layer when using for applying high level of the active ingredient on the contacting skin surface (this lamination type structure is especially useful when the active ingredient is chemically unstable or a drug which shows a potent pharmacological effect at minute amount or an expensive drug and it is used by linking the retaining means containing the active ingredient to the electrically conductive hydrophilic layer immediately before using). Further, the present device structure is not particularly limited to the method of constructing the device structure and that of strengthening the patch; composition of the backing or the backing structure including the electrodes.

The electrodes of the present invention are not particularly limited, provided that they are conductive materials for electrode which can be usually used for iontophoresis. These conductive materials include, e.g., silver, silver chloride, aluminum, zinc, copper, platinum, titan, stainless, as an inactive electrode. Among them, silver or silver/silver chloride as an active electrode has good electrical properties such as a resistance value as well as high manufacturing efficiency with a low cost when manufactured with a paste material. Inactive electrodes can be manufactured with a low cost by using carbon and the like as materials for the inactive electrode. Further, combination of them can be also used. On the other hand, the paste material is printed on the film for backing constituting the device structure. The printing methods include, e.g., screen printing. Electrode forms to be printed include multilayer printing wherein an active electrode is printed on an inactive electrode such as sheet-form, mesh-form, multi-layer printing and carbon, or these can be pattern-printed in various forms.

When using an inactive electrode for the device structure, gas generation can be suppressed by adding an electrode-reactive material to be oxidized or reduced at the voltage lower than that for water electrolysis. Such electrode-reactive materials include at least one or a combination of two or more selected from ascorbic acid, erysorbic acid, cystein, acetyl cystein, thioglycolic acid, thiomalic acid or their salts, sulfite, hydrogensulfite, thiosulfate, piosulfite, nitrite, iodide salts, and alpha thioglycerin at the anodic side, and at least one or a combination of two or more selected from ion (III) compounds such as iron (III) chloride, copper (II) compounds such as copper (II) sulfate and hydrogen peroxide. In the reaction with such electrode-reactive materials, hydrogen ions generate at the anodic side and hydroxide ions generate at the cathodic side, therefore as table device structure can be formed with controlling pH variation by use of these materials and the composition of the present invention.

In the structure for iontophoresis of the present inventions, pH of the electrically conductive layer at the anodic side is preferably adjusted to 3-9, more preferably pH 3-8, even more preferably pH 4-7 considering the drug dissolution, the drug safety and the skin stimulation.

Also at the cathodic side, pH of the electrically conductive layer is preferably adjusted to 3-9, more preferably pH 4-9, even more preferably 6-9 considering the skin stimulation and the drug dissolution during energizing by hydroxy ion present depending on pH of the conductive layer.

Specifically, the device structure comprising the electrically conductive layer of the present invention includes the following forms.

(1) A device structure for iontophoresis which administers at least one of active ingredients to be partially ionized through the skin or the mucosa to the body, provides an active electrode and an electrically conductive layer containing an active ingredient; wherein the above described active electrode comprises at least one of conductive metal materials selected from silver, copper, and zinc; the above described electrically conductive layer has a composition adjusted at pH 3-9 comprising the active ingredient, a chloride ion and a water swelling methacrylate copolymer; and the composition is composed of the following materials:

(a) the active ingredient is a cationic material, (b) the chloride ion is supplied from at least one of hydrochloric acid, hydrochloride salts and chlorides of the active ingredients, and (c) the water swelling methacrylate copolymer is a basic methacrylate copolymer or a mixture of a basic methacrylate copolymer and an acidic methacrylate copolymer.

(2) A device structure for iontophoresis which administers at least one of active ingredients to be partially ionized through the skin or the mucosa to the body, provides an active electrode and an electrically conductive layer containing an active ingredient; wherein the above described active electrode is at least selected from conductive metals including silver chloride; the above described electrically conductive layer has a composition adjusted at pH 3-9 comprising the active ingredient and a water swelling methacrylate copolymer; and the composition is composed of the following materials:

(a) the active ingredient is an anionic material, and (b) the water swelling methacrylate copolymer is an acidic methacrylate copolymer or a mixture of a basic methacrylate copolymer and an acidic methacrylate copolymer.

(3) A device structure for iontophoresis which administers at least one of active ingredients to be partially ionized through the skin or the mucosa to the body, provides an inactive electrode and an electrically conductive layer containing an active ingredient; wherein the above described inactive electrode comprises at least one conductive material selected from carbon, platinum and titanium; the above described electrically conductive layer has a composition adjusted at pH 3-8 comprising the active ingredient, the electrode-reactive material and a water swelling methacrylate copolymer; and the composition is composed of the following materials:

(a) the active ingredient is a cationic material, (b) the electrode-reactive material is at least one or a combination of two or more selected from ascorbic acid, erysorbic acid, cystein, acetyl cystein, thioglycolic acid, thiomalic acid or their salts, sulfite, hydrogensulfite, thiosulfate, piosulfite, nitrite, iodide salts, and alphathioglycerin, and (c) the water swelling methacrylate copolymer is a basic methacrylate copolymer or a mixture of a basic methacrylate copolymer and an acidic methacrylate copolymer.

(4) A device structure for iontophoresis which administers at least one of active ingredients to be partially ionized through the skin or the mucosa to the body, provides an inactive electrode and an electrically conductive layer containing an active ingredient; wherein the above described inactive electrode comprises at least one conductive material selected from carbon, platinum and titanium; the above described electrically conductive layer has a composition adjusted at pH 4-9 comprising the active ingredient, the electrode-reactive material and a water swelling methacrylate copolymer; and the composition is composed of the following materials:

(a) the active ingredient is an anionic material, (b) the electrode-reactive material is at least one or a combination of two or more selected from iron (III) compounds such as iron (III) chloride, copper (II) compounds such as copper (II) sulfate and hydrogen peroxide.

(c) the water swelling methacrylate copolymer is an acidic methacrylate copolymer or a mixture of a basic methacrylate copolymer and an acidic methacrylate copolymer.

When energizing with current using such device structure, the reference electrode structure comprising electrically conductive layer without containing a drug is usually used. Another form uses a method that the both electrodes contain a drug, that is, two sets of the device structure of the present invention are used and energized changing the polarity during energizing. Further, there is also the multipolarity-output method wherein the plural present device structure are used. The voltage or the electric current generated from the power source device connected with the electrode of the present device structure or the electrode of the reference electrode structure are usually controlled as constant-voltage or constant-current, preferably constant-current control to regulate the drug absorption. The electric current described herein means the transmission current related to the drug absorption. As the electric current generated from the power source, the direct current, the pulse current are used. As the power source can preferably apply the continuous direct voltage or the pulse direct voltage, more preferably apply the pulse directive voltage. The combination of them may be also used, further the intermittent energizing in which energizing and non-energizing are optionally set may be used. The power source which can apply square-shaped or diamond-shaped pulse direct voltage is particularly preferable. The frequency of the pulse direct voltage is optionally selected from the range of preferably 0.1-200 kHz, more preferably 1-100 kHz, most preferably 5-80 kHz. On/off ratio of the pulse direct voltage is optionally selected from the range of 1/100-20/1, preferably, 1/50-15/1, more preferably, 1/30-10/1. The average current density is 0.5 mA/cm$^2$ or less, preferably 0.1 mA/cm$^2$ or less, more preferably 0.05 mA/cm$^2$ or less being not particularly limited. Further, changing the current value optionally during energizing also enables to control the drug absorption rate.

In addition, although the device structure for iontophoresis of the present invention is generally applied to the skin, it can also be applied to the mucosa.

EXAMPLES

Examples and Comparative Examples of the present invention will be explained in details as follows, however, the present invention is not limited to these Examples. Hereinafter, "content" means "% (w/w)" unless otherwise specified.

Experimental Example 1

A Preparation Example when Aminoalkylmethacrylate Copolymer E is Used as a pH Adjusting Agent Experimental Example 1 shows a preparation example when aminoalkylmethacrylate copolymer E is used as a pH adjusting agent. The pH of a preparation in this Experimental Example was adjusted to around 4.5-6.5. In this step, hydrochloric acid was charged to add chloride ion as a reactant with an active electrode.

Example 1

| Component | Content (%(w/w)) |
| --- | --- |
| Fentanyl citrate | 1.00 |
| Agar | 1.00 |
| Aminoalkylmethacrylate copolymer E | 5.60 |
| Hydrochloric acid | 0.55 |
| Methyl para-oxybenzoate | 0.20 |
| Distilled water for injection | Appropriate amount |
| Total | 100.00 |

Fentanyl citrate, aminoalkylmethacrylate copolymer E and hydrochloric acid were added to distilled water and stirred until these were dissolved. Further, agar and methyl para-oxybenzoate were added with stirring followed by heating at about 90° C. to dissolve. After cooled near to about 60° C., about 0.8 g of this solution was charged into an electrode cup made of polyethylene terephthalate (therein after, abbreviated as PET). The pH of the prepared formulation was 4.9.

Comparative Example 1

| Component | Content (%(w/w)) |
| --- | --- |
| Fentanyl citrate | 1.00 |
| Agar | 1.00 |
| Hydrochloric acid | 0.55 |
| Methyl para-oxybenzoate | 0.20 |
| Distilled water for injection | Appropriate amount |
| Total | 100.00 |

Fentanyl citrate and hydrochloric acid were added to distilled water with stirring. Further, agar and methyl para-oxybenzoate were added with stirring followed by heating at about 90° C. to dissolve. After cooled near to about 60° C., about 0.8 g of this solution was charged into an electrode cup made of PET. The pH of the prepared formulation without gelation was 1 or less.

Comparative Example 2

| Component | Content (%(w/w)) |
|---|---|
| Fentanyl citrate | 1.00 |
| Agar | 1.00 |
| Meglumine | 3.60 |
| Hydrochloric acid | 0.55 |
| Methyl para-oxybenzoate | 0.20 |
| Distilled water for injection | appropriate amount |
| Total | 100.00 |

Fentanyl citrate, meglumine and hydrochloric acid were added to distilled water with stirring. Further, agar and methyl para-oxybenzoate were added with stirring followed by heating at about 90° C. to dissolve. After cooled near to about 60° C., about 0.8 g of this solution was charged into an electrode cup made of PET. The pH of the prepared formulation was 4.8.

Experimental Example 2

Figure 2:
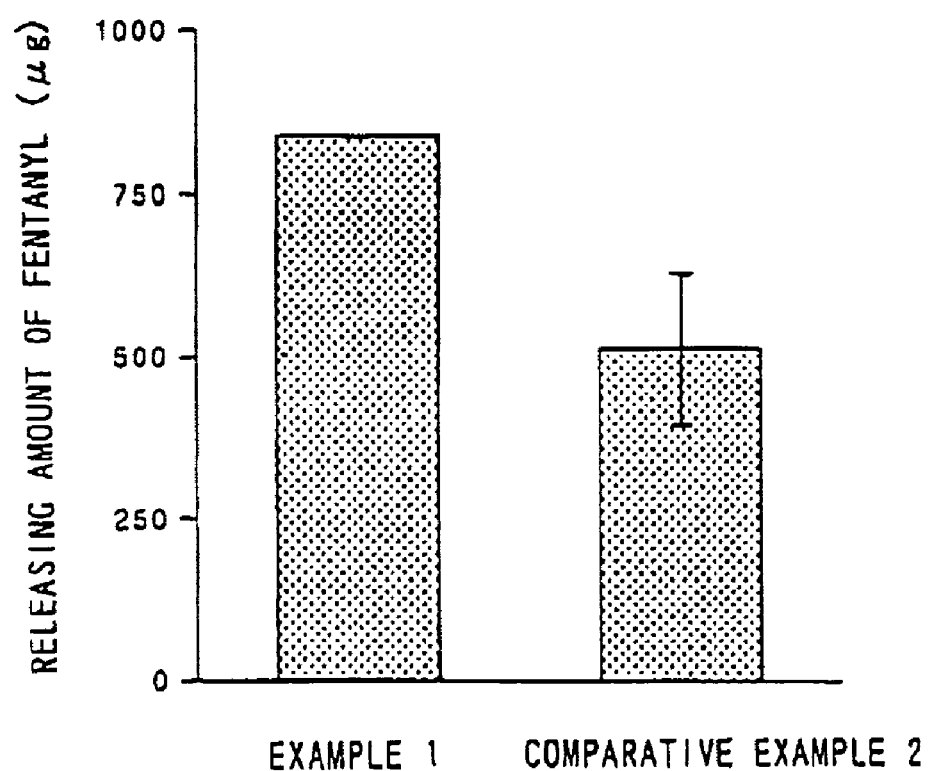
FIG. 2 is a graph showing the results of the releasing test of fentanyl citrate by iontophoresis.

Influence of aminoalkylmethacrylate Copolymer E Affecting an Iontophoresis-Releasing Test of Fentanyl Citrate Next, using the above described formulations (Example 1 and Comparative Example 2), a releasing test by iontophoresis was performed. Using a sideways type cell in the releasing test, 3% (w/w) agarose gel (3 mm) was used as a release control layer. The experiment was conducted at a room temperature, and after electrically energizing with current for 1 hr, the drug amount transferred into a receptor layer was measured by high-performance liquid chromatography. The electrically energizing with current was performed at 0.2 mA/cm$^2$ constant-current for 1 hr of the total energizing time using direct-current energizing for pulse depolarization (50 kHz frequency, 50% duty) by a short-circuit switch. FIG. 2 is a graph showing the results of the releasing test of fentanyl citrate by iontophoresis. As clarified from FIG. 2, the releasing amount of fentanyl by ionyophoresis is higher in Example 1 than that in Comparative Example 2 so that aminoalkylmethacrylate copolymer E was effective as a pH adjusting material.

Experimental Example 3

An Absorption Test Using Rats in a Device Structure of the Present Invention Using an Active Electrode In Experimental Example 3, the absorbable evaluation of the preparation of Example 2 was performed as an example of the device structure using the active electrode of the present invention. As for the electrode, a silver foil electrode (18 mm in the inside diameter) was loaded into a cup-shaped molded container (PET-made, 30 mm in the inside diameter, 7.07 cm$^2$ of the effective area) and then 1.3 g gel of the preparation shown in Example was charged. A hydrophilic porous membrane (made by Nihon Millipore Ltd., DURAPORE, 9.62 cm$^2$) was further provided as an absorption control membrane. In this absorption using rats, SD males (about 250 g weight) were used after treatment for shaving fur of the back skin by hair clippers and a shaver. Two sheets of the above described electrode device structure were stuck on the back skin of each rat. The electrically energizing with current was performed at 0.05 mA/cm$^2$ constant-current for 30 min of polarity reverse time and for 5 hr of the total energizing time using direct-current energizing for pulse depolarization (50 kHz frequency, 50% duty) by a short-circuit switch. Collecting blood in each time course, the drug level in plasma was measured by HPLC. Consequently, it was confirmed that the drug level in plasma showed high absorption for a long time (the drug level in plasma for 2-5 hr during electrically energizing time: about 2,000 ng/ml).

Example 2

| Component | Content (%(w/w)) |
|---|---|
| TAK-024 | 2.9 |
| Agarose | 1.0 |
| Aminoalkylmethacrylate copolymer E | 1.2 |
| Proline | 10.0 |
| Distilled water for injection | Appropriate amount |
| Total | 100.0 |

TAK-024 and aminoalkylmethacrylate copolymer E were added to distilled water with stirring. Further, proline and agarose were added with stirring followed by heating at about 90° C. After cooled near to about 60° C., about 1.3 g of this solution was charged into an electrode cup made of PET. The pH of the prepared formulation was 4.5. The chemical formula of TAK-024 used herein is shown as follows.

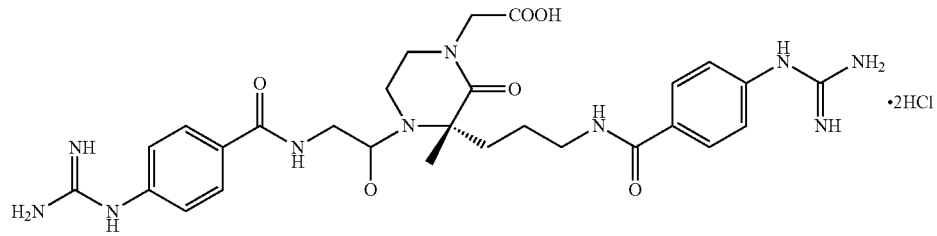

Experimental Example 4

Investigation of the pH Changes and the Skin Stimulation in the Device Structure of the Present Invention Using an Inactive Electrode Experimental Example 4 as an example of the device structure of the present invention using an inactive electrode was investigated for the in vivo pH changes of the preparations of Example 3 and Comparative Example 3. After SD rats (males, about 250-300 g weight) were treated for shaving fur of the abdominal skin by hair clippers and a shaver, the skin was used conducting defatted disinfect using absorbent cotton containing 70% ethanol in water. As for the electrode, a carbon electrode (18 mm in the inside diameter) was loaded into a cup-shaped molded container (PET-made, 25 mm in the inside diameter, 4.9 cm$^2$ of the effective area) and then 0.7 g gel of the preparation shown in Example was charged to form the electrode structure. Electrically energizing was started using an agar gel containing 3% (w/w) sodium chloride as a reference electrode. The electrically energizing with current was performed at 0.1 mA/cm$^2$ constant-current for 4 hr of the total energizing time using direct-current energizing for pulse depolarization (50 kHz frequency, 50% duty) by a short-circuit switch. After completion of the experiment, the pH of the preparation and the skin stimulation were observed.

Example 3

| Component | Content (%(w/w)) |
| --- | --- |
| Lidocaine hydrochloride | 2.0 |
| Agar | 1.0 |
| Aminoalkylmethacrylate copolymer E | 12.0 |
| Methyl para-oxybenzoate | 0.2 |
| Ascorbic acid | 1.7 |
| Distilled water for injection | Appropriate amount |
| Total | 100.0 |

Lidocaine hydrochloride, Aminoalkylmethacrylate copolymer E and Ascorbic acid were added to distilled water with stirring to dissolve. In addition, agar and Methyl para-oxybenzoate were added with stirring followed by heating at about 90° C. After cooled near to about 60° C., about 0.7 g of this solution was charged into an electrode cup made of PET. The pH of the prepared formulation was 6.8.

Comparative Example 3

| Component | Content (%(w/w)) |
| --- | --- |
| Lidocaine hydrochloride | 2.0 |
| Agar | 1.0 |
| Methyl para-oxybenzoate | 0.2 |
| Distilled water for injection | Appropriate amount |
| Total | 100.0 |

Lidocaine hydrochloride, agar and Methyl para-oxybenzoate were added to distilled water with stirring followed by heating at about 90° C. to dissolve. After cooled near to about 60° C., about 0.7 g of this solution was charged into an electrode cup made of PET. The pH of the prepared formulation was 5.3.

Consequently, the pH after completion of electrically energizing was 6.6 at Example 3 and 0.8 at Comparative Example 3. A rapid decrease phenomenon of the pH based on the preparation of Comparative Example 3 was observed by accompanying with generation of hydrogen ions during energizing with current, while the pH retaining effect was recognized by adding aminoalkylmethacrylate copolymer E of Example 3. Since ascorbic acid as a depolarizer in Example 3 was added, no generation of oxygen gas was also recognized during energizing with current. Further, in Comparative Example 3, blister formation on surface of the skin was observed together with strong skin stimulation, while the stimulation was not almost recognized in Example 3.

Experimental Example 5

The pH Changes when Aminoalkylmethacrylate Copolymer E and a Weakly Acidic Material Were Used as pH Adjusting Agents In experimental Example 5, the pH changes were investigated when aminoalkylmethacrylate copolymer E and a weakly acidic material were used as pH adjusting agents. In such cases that the pH decreases in the acidic side (especially in many drugs of hydrochloride salts) when a drug is dissolved in aqueous solution; and the pH decreased by adding hydrochloric acid to react with an active electrode and the like, the pH of the preparation varies depending on error of a minute adding amount of a pH adjusting agent when adjusting the pH by using aminoalkylmethacrylate copolymer E. In order to regulate such scattering at preparation and storage, a buffer is further added in the preparation.

Figure 3:
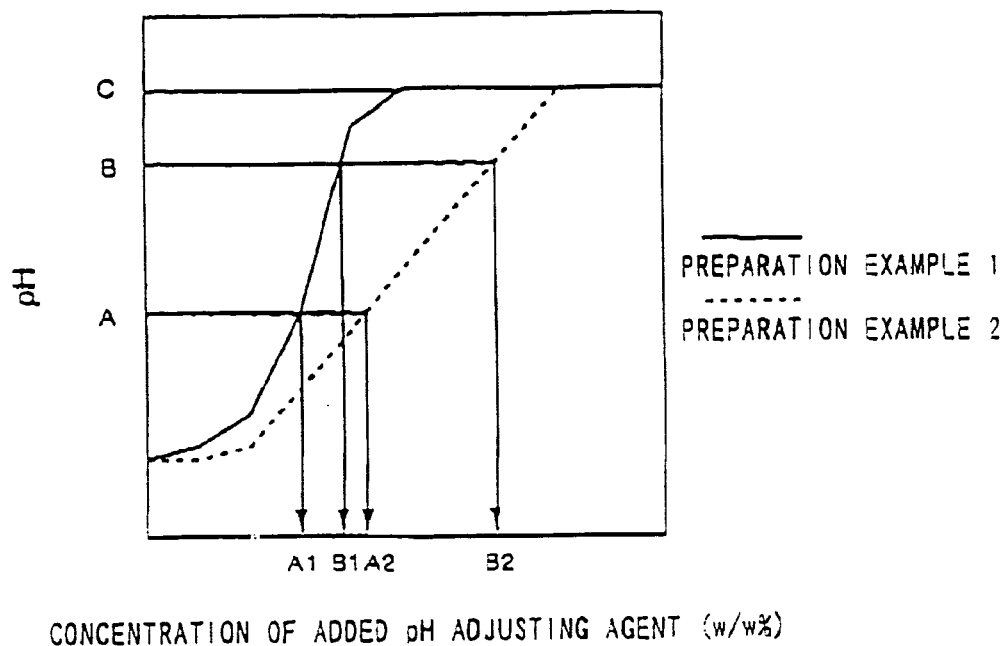
FIG. 3 is a graph showing examples of the pH adjustment using a basic methacrylate copolymer and weakly acidic materials.

FIG. 3 is a graph showing a pH adjusting agent using a basic methacrylate copolymer and a weakly acidic material. For example, as shown in FIG. 3, when set the finally adjusting pH to A-B, the adding concentration of the pH adjusting agent in preparation example 1 (a solid line) should be added within the range of A1-B1 (% (w/w)). However, in preparation example 2 (a broken line) in which an acidic material is added in the preparation, concentration of the pH adjusting agent becomes A2-B2 (% (w/w)). Specifically, the adding concentration in each preparation example is: difference between B1 and A1 (preparation example 1)<difference between B2 and A2 (preparation example 2); the pH adjusting system such as preparation example 2 does not be influenced based on the changes of concentration of the added pH adjusting agent, leading to be capable of preparing the stable performance with less pH changes during preparation and storage.

Figure 4:
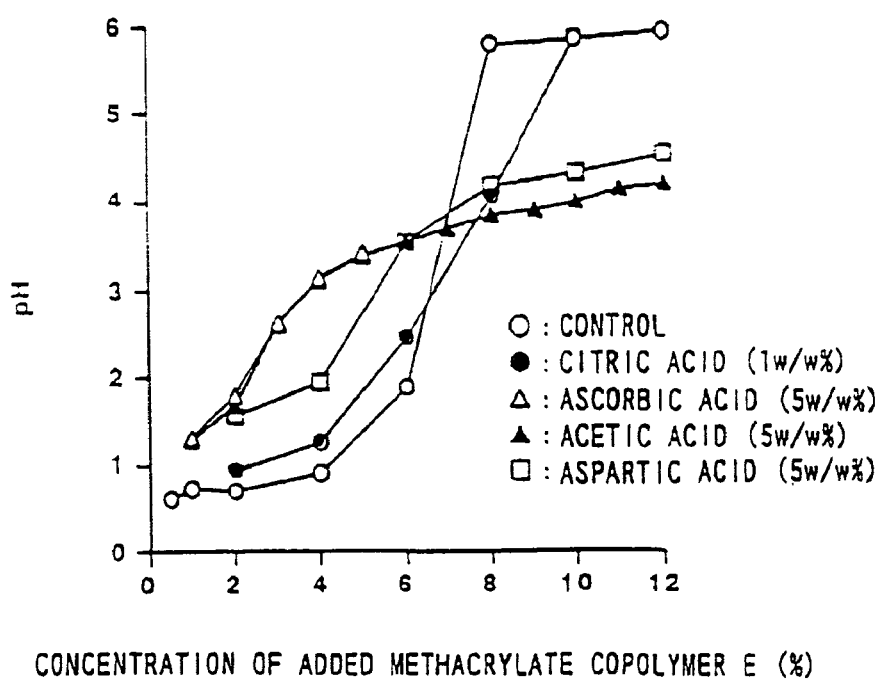
FIG. 4 is a graph showing relationship between the concentration of an added basic methacrylate copolymer and the pH when using various weakly acidic materials.

FIG. 4 is a graph showing relationship between the adding concentration of a basic methacrylate copolymer and the pH when used various weakly acidic materials. This Figure shows influence of different weakly acidic materials which affect the pH adjusting effect by aminoalkylmethacrylate copolymer E in the presence of hydrochloric acid (0.75%). The control is the one which the pH is adjusted by aminoalkylmethacrylate copolymer E alone without addition of weakly acidic materials. By adding weakly acidic materials such as citric acid, acetic acid, aspartic acid and ascorbic acid, the rapid pH change, as observed in the control, by adding aminoalkylmethacrylate copolymer E was controlled.

Experimental Example 6

The pH Changes when Aminoalkylmethacrylate Copolymer E and Methacrylate Copolymer L were used as pH Adjusting Agents In experimental Example 6, the pH changes were investigated when aminoalkylmethacrylate copolymer E and methacrylate copolymer L were used as pH adjusting agents. This case shows the pH adjusting region mainly at near C in FIG. 3 and these agents are used for regulating the pH changes with electrically energizing with current. For example, an acidic methacrylate copolymer is preferably added at the anodic side (the pH adjusting region is at near C or more in FIG. 3) and also a basic methacrylate copolymer is preferably added at the cathodic side (the pH adjusting region is at near C in FIG. 3 or more than that) in dispersive condition (suspension). When 0.1 to 10% (w/w) methacrylate copolymer L was added into a preparation containing 1% (w/w) hydrochloric acid, 0.1% (w/w) fentanyl and 10% (w/w) aminoalkylmethacrylate copolymer E, the adjusted pH was constant at near 6-7.

Example 4

| Component | Content (%(w/w)) |
| --- | --- |
| Fentanyl citrate | 0.1 |
| Agar | 1.0 |
| Aminoalkylmethacrylate copolymer E | 4.5 |
| Methacrylate copolymer L | 4.5 |
| Hydrochloric acid | 0.5 |
| Methyl para-oxybenzoate | 0.2 |
| Distilled water for injection | Appropriate amount |
| Total | 100.0 |

Fentanyl citrate, aminoalkylmethacrylate copolymer E, methacrylate copolymer L and hydrochloric acid were added to distilled water with stirring. Further, agar and methyl para-oxybenzoate were added with stirring followed by heating at about 90° C. After cooled near to about 60° C., about 0.8 g of this solution was charged into an electrode cup made of PET. The pH of the prepared formulation was 6.3.

Using the preparation of Example 4, iontophoresis was conducted to rabbits. In this experiment, after Japanese white rabbit males (about 3.0-4.0 kg in weight) were treated for shaving fur of the back skin by hair clippers and a shaver, the skin was used conducting mildly scraping and defatted disinfect using absorbent cotton containing 70% ethanol in water. The donor preparation was stuck on the back skin of rabbits, and electrically energizing was started using an agar gel containing 3% (w/w) sodium chloride as a reference electrode. The electrically energizing with current was performed at 0.1 mA/cm$^2$ constant-current for 4 hr of the total energizing time using direct-current energizing for pulse depolarization (50 kHz frequency, 50% duty) by a short-circuit switch. Consequently, the pH was 6.5 after completion of the electrically energizing, and the pH changes before or after completion of the electrically energizing, was not observed at all. In the case that the pH was adjusted by meglumine without addition of the acidic methacrylate copolymer, the pH was elevated from 4.8 to 5.8.

According to the composition for iontophoresis of the present invention, the composition includes the following properties by using a water swelling polymer having a pH adjusting function: giving the optimum preparation to various active ingredients without reduction of the delivery rate of the active ingredients (drugs)); further being capable of regulating the pH changes during energizing with current; and being capable of retaining the stable absorption for a long time. In addition, by regulating the scattering of pH, uniformity, dispersibility and pH changes during energizing with current at manufacturing, the composition for iontophoresis having the following characteristics is also obtained: good energizing property with current for a long time; efficiently stable drug absorption; and further excellent safety to the living body. Further, the device structure using it gives high bioavailability of active ingredients and is excellent in general use and practical use, in either an active electrode or inactive electrode material.

What is claimed is:

1. A device structure for iontophoresis which administers at least one of active ingredients to be partially ionized through the skin or the mucosa to the body, provides an active electrode and an electrically conductive layer containing an active ingredient; wherein the above described active electrode comprises at least one of conductive metal materials selected from silver, copper, and zinc; the above described electrically conductive layer has a composition adjusted at pH 3-9 comprising the active ingredient, a chloride ion and a water swelling methacrylate copolymer having a pH adjusting function; and the composition is composed of the following materials:
   (a) the active ingredient is a cationic material,
   (b) the chloride ion is supplied from at least one of hydrochloric acid, hydrochloride salts and chlorides of the active ingredients, and
   (c) the water swelling methacrylate copolymer is a basic methacrylate copolymer or a mixture of a basic methacrylate copolymer and an acidic methacrylate copolymer.

2. A device structure for iontophoresis which administers at least one of active ingredients to be partially ionized through the skin or the mucosa to the body, provides an active electrode and an electrically conductive layer containing an active ingredient; wherein the above described active electrode is at least selected from conductive metals including silver chloride; the above described electrically conductive layer has a composition adjusted at pH 3-9 comprising the active ingredient and a water swelling methacrylate copolymer having a pH adjusting function; and the composition is composed of the following materials:
   (a) the active ingredient is an anionic material, and
   (b) the water swelling methacrylate copolymer is an acidic methacrylate copolymer or a mixture of a basic methacrylate copolymer and an acidic methacrylate copolymer.

3. A device structure for iontophoresis which administers at least one of active ingredients to be partially ionized through the skin or the mucosa to the body, provides an inactive electrode and an electrically conductive layer containing an active ingredient; wherein the above described inactive electrode comprises at least one conductive material selected from carbon, platinum and titanium; the above described electrically conductive layer has a composition adjusted at pH 3-8 comprising the active ingredient, the electrode-reactive material and a water swelling methacrylate copolymer having a pH adjusting function; and the composition is composed of the following materials:
   (a) the active ingredient is a cationic material,
   (b) the electrode-reactive material is at least one or a combination of two or more selected from ascorbic acid, erysorbic acid, cystein, acetyl cystein, thioglycolic acid, thiomalic acid or their salts, sulfite, hydrogensulfite, thiosulfate, piosulfite, nitrite, iodide salts, and alphathioglycerin, and
   (c) the water swelling methacrylate copolymer is a basic methacrylate copolymer or a mixture of a basic methacrylate copolymer and an acidic methacrylate copolymer.

4. A device structure for iontophoresis which administers at least one of active ingredients to be partially ionized through the skin or the mucosa to the body, provides an inactive electrode and an electrically conductive layer containing an active ingredient; wherein the above described inactive electrode comprises at least one conductive material selected from carbon, platinum and titanium; the above described electrically conductive layer has a composition adjusted at pH 4-9 comprising the active ingredient, the electrode-reactive material and a water swelling methacrylate copolymer having a pH adjusting function; and the composition is composed of the following materials:

(a) the active ingredient is an anionic material,
(b) the electrode-reactive material is at least one or a combination of two or more selected from iron (III) compounds, copper (II) compounds and hydrogen peroxide,
(c) the water swelling methacrylate copolymer is an acidic methacrylate copolymer or a mixture of a basic methacrylate copolymer and an acidic methacrylate copolymer.

* * * * *